US00RE41615E

(19) United States
(12) Reissued Patent
Kim et al.

(10) Patent Number: US RE41,615 E
(45) Date of Reissued Patent: Aug. 31, 2010

(54) CROSSLINKED, WATER-SOLUBLE OR WATER-DISPERSIBLE POLYURETHANES

(75) Inventors: Son Nguyen Kim, Hemsbach (DE); Axel Sanner, Frankenthal (DE); Peter Hössel, Schifferstadt (DE); Volker Schehlmann, Schifferstadt (DE)

(73) Assignee: BASF SE, Ludwigshafen (DE)

(21) Appl. No.: 11/165,555

(22) Filed: Jun. 24, 2005

Related U.S. Patent Documents

Reissue of:
(64) Patent No.: 6,262,176
Issued: Jul. 17, 2001
Appl. No.: 09/303,426
Filed: May 3, 1999

(30) Foreign Application Priority Data

May 14, 1998 (DE) ..... 198 21 732

(51) Int. Cl.
*C08G 18/62* (2006.01)

(52) U.S. Cl. ..... 525/127; 424/47; 424/61; 424/70.1; 424/70.11; 424/78.02; 424/78.3; 514/772.1; 524/832; 524/833; 524/840; 525/128; 528/62

(58) Field of Classification Search ..... 524/507, 524/591, 839, 840, 47, 61, 70.1, 70.11, 78.02, 524/78.3, 832, 833; 525/127, 128; 514/772.1; 528/62

See application file for complete search history.

(56) References Cited

U.S. PATENT DOCUMENTS

| | | | | |
|---|---|---|---|---|
| 3,927,199 | A | 12/1975 | Micchelli et al. | 424/47 |
| 5,480,936 | A | 1/1996 | Duecoffre et al. | 524/839 |
| 5,612,404 | A | 3/1997 | Das et al. | 524/507 |
| 5,643,581 | A | 7/1997 | Mougin et al. | 424/401 |
| 6,090,871 | A | 7/2000 | Reiners et al. | 524/27 |
| 6,335,003 | B1 | 1/2002 | Kim et al. | 424/71.17 |
| 6,365,697 | B1 | 4/2002 | Kim et al. | 528/28 |
| 6,368,583 | B1 | 4/2002 | Kim et al. | 424/70.122 |
| 6,372,876 | B1 | 4/2002 | Kim et al. | 528/71 |
| 6,395,265 | B1 | 5/2002 | Mougin et al. | 424/70.12 |
| 6,579,517 | B1 * | 6/2003 | Kim et al. | 424/70.12 |

FOREIGN PATENT DOCUMENTS

| | | |
|---|---|---|
| DE | 4225045 | 7/1992 |
| DE | 4241118 | 12/1992 |
| DE | 42 25 045 | 3/1994 |
| DE | 42 41 118 | 9/1994 |
| DE | 19541329 | 6/1995 |
| DE | 19541326 | 5/1997 |
| DE | 195 41 326 | 7/1997 |
| DE | 195 41 329 | 7/1997 |
| EP | 389386 | 3/1989 |
| EP | 0 389 386 | 9/1990 |
| EP | 687459 | 6/1994 |
| EP | 619111 | 10/1994 |
| EP | 0 319 111 | 11/1994 |
| EP | 773246 | 8/1995 |
| EP | 0 687 459 | 12/1995 |
| EP | 0 741 156 | 11/1996 |
| EP | 0 773 246 | 5/1997 |
| JP | H5/295078 | 11/1993 |
| WO | WO 94/03515 | 2/1994 |
| WO | WO 96/30425 | 10/1996 |
| WO | WO 97/00664 | 1/1997 |
| WO | WO 97/17052 | 5/1997 |
| WO | WO 97/17386 | 5/1997 |
| WO | WO 97/22632 | 6/1997 |
| WO | WO 97/23519 | 7/1997 |
| WO | WO 97/23527 | 7/1997 |
| WO | WO 97/25021 | 7/1997 |

* cited by examiner

*Primary Examiner*—John Cooney
(74) *Attorney, Agent, or Firm*—Novak Druce + Quigg LLP

(57) ABSTRACT

The present invention relates to crosslinked, water-soluble or water-dispersible polyurethanes of A) at least one water-soluble or water-dispersible polyurethane prepolymer having terminal isocyanate groups of
   a) at least one compound having a molecular weight in the range from 56 to 300 which contains two active hydrogen atoms per molecule,
   b) at least one polymer containing two active hydrogen atoms per molecule,
   c) at least one compound which contains two active hydrogen atoms and at least one ionogenic or ionic group per molecule,
   d) at least one diisocyanate, B) at least one polymer containing groups which are reactive toward isocyanate groups, chosen from hydroxyl, and primary and secondary amino and/or carboxyl groups, or the salts thereof.

7 Claims, No Drawings

CROSSLINKED, WATER-SOLUBLE OR WATER-DISPERSIBLE POLYURETHANES

Matter enclosed in heavy brackets [ ] appears in the original patent but forms no part of this reissue specification; matter printed in italics indicates the additions made by reissue.

The present invention relates to crosslinked, water-soluble or water-dispersible polyurethanes of at least one polyurethane prepolymer containing terminal isocyanate groups and at least one polymer containing groups which are reactive toward isocyanate groups, chosen from hydroxyl, and primary and secondary amino- and/or carboxyl groups.

In cosmetics, polymers with film-forming properties are used for setting, shaping and improving the structure of the hair. These hair treatment compositions generally contain a solution of the film former in an alcohol or in a mixture of alcohol and water.

Hairsetting compositions are generally sprayed on the hair in the form of aqueous-alcoholic solutions. Following the evaporation of the solvent, the individual hairs are held in the desired shape at their points of mutual contact by the polymer which is left behind. The polymers should on the one hand be sufficiently hydrophilic that they can be washed out of the hair, yet on the other hand should be hydrophobic so that the hair treated with the polymers retains its shape even under conditions of high atmospheric humidity, and the individual hairs do not stick to one another. In order to obtain a highly efficient hairsetting effect, moreover, it is also desirable to employ polymers which have a relatively high molecular weight and a relatively high glass transition temperature (at least 15° C.).

A further consideration when formulating hairsetting agents is that because of the environmental regulations governing the emission of volatile organic compounds (VOCs) into the atmosphere it is necessary to reduce the content of alcohol and of propellant.

A further current demand on hair treatment compositions is that they should give the hair a natural appearance and luster even, for example, when the hair concerned is by its very nature particularly strong and/or dark.

DE-A-42 25 045 and WO 94/03515 describe uncrosslinked, water-so-luble or water-dispersible polyurethanes which comprise, in copolymerized form, at least 5 mol % of a polycondensate of lactic acid and a polyol, and also the use of water-soluble or water-dispersible polyurethanes of a) at least one compound which contains two or more active hydrogen atoms per molecule, b) at least one diol containing acid or salt groups and c) at least one diisocyanate, as auxiliary in cosmetic and pharmaceutical preparations.

DE-A-42 41 118 describes the use of uncrosslinked, cationic polyurethanes and polyureas as auxiliaries in cosmetic and pharmaceutical preparations.

EP-A-619 111 describes the use of polyurethanes based on organic diisocyanates, diols and 2,2-hydroxymethyl-substituted carboxylates of the formula

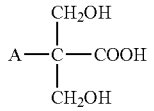

where A is a hydrogen atom or a $C_1$–$C_{20}$-alkyl group in hair fixatives. In this case at least some of the carboxyl groups are neutralized with an organic or inorganic base. Films based on these linear polyurethanes have little flexibility and are thus in need of improvement.

EP-A-636 361 describes a cosmetic composition comprising, in a cosmetically compatible vehicle, at least one pseudolatex based on a polycondensate which comprises at least one polysiloxane unit and at least one polyurethane and/or polyurea unit having anionic or cationic groups. Crosslinked, water-soluble or water-dispersible polyurethanes are not described. The disclosure content of WO 97/25021 is similar. These cosmetic compositions are suitable, inter alia, for treating keratinous materials. The ease of washout of these film formers, however, is unsatisfactory. In addition, their high siloxane content robs them of the setting effect also required of a hair polymer.

DE-A-195 41 329 and WO 97/17052 describe hair treatment compositions comprising a salt which is dispersible or soluble in water and has the formula I $$[A—(X)_n]^{n-}[H_mB]^{m+} \qquad \text{I}$$

where

A is a cosmetically acceptable aliphatic, cycloaliphatic or aromatic radical, which may have siloxane-containing units and/or fluorine-containing units, X is a carboxylate, sulfonate, phosphate or phosphonate group;

B is a cosmetically acceptable amine base which may comprise siloxane-containing and/or fluorine-containing units;

n is from 1 to 30; and m is the valence of the amine B.

Hairspray formulations based on these siloxane-containing salts, lead to films which are easily removed from the surface of the hair by mechanical stress, for example. The setting effect of these formulations is therefore in need of improvement.

DE-A-195 41 326 and WO 97/17386 describe water-soluble or water-dispersible polyurethanes having terminal acid groups, their preparation and their use. In this case a polyurethane prepolymer which is dispersible or soluble in water and has terminal isocyanate groups is reacted with an aminosulfonic or aminocarboxylic acid, especially taurine, aspartic acid and glutamic acid. Hairsprays based on these polyurethanes are still in need of improvement. Problems may occur in particular when formulating hairsprays having a high content of propellant gas and/or a high content of organic solvents and, if appropriate, with the simultaneous use of spray atomizers for obtaining very small droplets.

EP-A-0 389 386 describes linear diorganopolysiloxane-polyester block copolymers containing incorporated urethane units, which are suitable for the controlled release of pharmaceutical preparations.

EP-A-0 626 432 describes thermally curable coating compositions of a polyester oligomer-polyacrylate containing free OH groups and at least one polyisocyanate containing free NCO groups, and their use for the preparation of clearcoats. Once crosslinked, these polymers are neither water-soluble nor water-dispersible and are unsuitable for the preparation of cosmetic preparations.

WO 97/00664 describes an aqueous nail polish comprising a bifunctional urethane acrylate oligomer crosslinked with an acrylic resin. Polyurethanes of at least one polyurethane prepolymer containing terminal isocyanate groups are not described. The films resulting from these compositions are water-resistant and not redispersible. They are not suitable for use in cosmetic compositions for use on skin or hair.

EP-A-0 687 459 describes hair treatment compositions based on an aqueous polymer dispersion obtainable by free-radical graft copolymerization of a monoethylenically unsaturated siloxane macromonomer and at least one polyurethane and/or polyurea copolymer. Crosslinked polyurethanes of polyurethane prepolymers containing terminal isocyanate groups and polymers containing groups which are reactive toward isocyanate groups are not described in this document.

U.S. Pat. No. 3,927,199 describes a hairsetting composition based on a copolymer comprising, in copolymerized form, (1) from 30 to 60% by weight of an N-($C_2$- to $C_{12}$)-alkyl (meth)acrylamide, (2) from 12 to 18% by weight of an α,β-ethylenically unsaturated acid-group-containing comonomer, (3) from 20 to 55% by weight of at least one comonomer chosen from alkyl (meth)acrylates, hydroxyalkyl (meth)acrylates, vinyl acetate, vinyl propionate, diacetone acrylamide, styrene and α-methylstyrene. Neutralization with a base gives a copolymer which is water-soluble or -dispersible and is suitable for formulating hair sprays. Crosslinked polyurethanes based on polyurethane prepolymers containing terminal isocyanate groups are not described in this document. These hairsetting compositions exhibit a sharp increase in viscosity in aqueous formulations with increasing water content and are unsuitable for the preparation of products having a low content of VOC.

WO 97/23519 describes anionic amino-containing polymers obtainable by free-radical polymerization of olefinic amino-containing monomers in an aqueous medium in the presence of an azo initiator. The initiator has neutralized carboxyl groups. The amino-containing monomers are, for example, amino (meth)acrylates, such as tert-butylaminoethyl (meth)acrylate. The polymers may further contain olefinically unsaturated monomers, such as (meth) acrylic esters and hydroxyalkyl (meth)acrylates, in copolymerized form. They are suitable for the preparation of single- or two-component coating compositions, for the coating of metallic and plastic surfaces, which are cured by crosslinking with polyisocyanates or polyepoxides. Crosslinked, water-soluble or water-dispersible polymers which are suitable for use as or in a cosmetic composition are not described. Polymers which contain, in copolymerized form, an aminoalkyl (meth)acrylate in an amount of from 0.1 to 10% by weight and their use as intermediates for the preparation of crosslinked, water-soluble or water-dispersible polyurethanes are likewise not described.

WO 97/23527 describes an aqueous single-component coating composition based on a polyurea binder comprising a polymer containing primary and/or secondary amino groups which are reactive toward isocyanate groups and which may additionally have hydroxyl groups, and a polyisocyanate. The amino-containing polymers comprise, in copolymerized form, (1) at least one olefinically unsaturated monomer containing primary or secondary amino groups, e.g. an aminoalkyl (meth)acrylate, (2) optionally a hydroxyl-containing monomer, e.g. a hydroxyalklyl (meth)acrylate, (3) optionally other olefinically unsaturated monomers, chosen from (meth)acrylic esters, styrene, alkylstyrenes, (meth) acrylonitrile, vinyl acetate etc. The binders which result from crosslinking with the polyurethane are suitable for coating metallic and plastic surfaces. Crosslinked, water-soluble or water-dispersible polyurethanes are not described. Polymers comprising, in copolymerized form, from 0.1 to 10% by weight of at least one monomer containing a primary and/or secondary amino group and their use as intermediates for the preparation of crosslinked, water-soluble or water-dispersible polyurethanes are likewise not described.

U.S. Pat. No. 5,612,404 has a disclosure content corresponding to WO 97/23519 and WO 97/23527.

WO 96/30425 describes an aqueous two-component polyisocyanate coating composition based on an essentially isocyanate-free emulsifier, comprising a reaction product of: (1) an isocyanate and (2) a component chosen from hydroxyl-containing polyalkyl ethers containing at least 5 ethylene oxide units, including various alcohols, amino compounds and mixtures thereof. The binders containing groups reactive toward isocyanate groups may be the polymers based on amino alkyl (meth)acrylates described in WO 97/23527.

WO 97/22632 describes a process for the preparation of an adhesive composition comprising:

(a) reacting a diol or polyol with a diisocyanate to give a prepolymer containing terminal isocyanate groups;

(b) reacting the first prepolymer to convert at least some of the terminal isocyanate groups into terminal methacrylate groups, e.g. with an aminoalkyl (meth) acrylate, such as N-tert-butylaminoethyl methacrylate;

(c) reacting the residual isocyanate groups with a stopper, preferably an alkanolamine, such as triethanolamine;

(d) thermal or photochemical curing of the prepolymer from (c) to form a polyurethane (meth)acrylate-based adhesive. The resulting adhesives are pressure-sensitive and are suitable for use on the skin, e.g. in medical products for the dressing of wounds.

Crosslinked, water-soluble or water-dispersible polyurethanes of a polyurethane prepolymer and a polymer containing groups reactive toward isocyanate groups are not described in this document.

EP-A-0 773 246 describes water-soluble or water-dispersible graft polymers of

A) a water-soluble or -dispersible polyurethane prepolymer containing terminal isocyanate groups and B) a protein containing free amino groups.

These are suitable as auxiliaries in cosmetics and, in particular, as hairsetting agents with improved washout. A disadvantage with using proteins is that they require stabilization by preservatives and, being natural substances, frequently have fluctuating product properties.

It is an object of the present invention to provide novel polyurethanes, in particular for hair treatment compositions, which, on the one hand, can be used as hairsetting agent, but on the other hand, also have good washout (redispersibility). They should preferably form smooth and flexible films.

Surprisingly, we have found that this object is achieved by crosslinked, water-soluble or water-dispersible polyurethanes which are the reaction product of at least one polyurethane prepolymer containing terminal isocyanate groups and at least one polymer containing groups which are reactive toward isocyanate groups.

The present invention thus provides crosslinked, water-soluble or water-dispersible polyurethanes of A) at least one water-soluble or water-dispersible polyurethane prepolymer containing terminal isocyanate groups of a) at least one compound having a molecular weight in the range from 56 to 300 which contains two active hydrogen atoms per molecule, b) at least one polymer containing two active hydrogen atoms per molecule, c) at least one compound which contains two active hydrogen atoms and at least one ionogenic or ionic group per molecule, d) at least one diisocyanate, B) at least one polymer containing groups which are reactive toward isocyanate groups, chosen from hydroxyl, and primary and secondary amino and/or carboxyl groups, or the salts thereof.

Component a) is preferably a diol, diamine, aminoalcohol, or a mixture thereof. The molecular weight of these compounds is preferably in a range from about 56 to 280. If desired, up to 3 mol % of said compounds can be replaced by triols or triamines.

Diols are preferably used as component a). Diols which can be used are, for example, ethylene glycol, propylene glycol, butylene glycol, neopentyl glycol, cyclohexanedimethylol, di-, tri-, tetra-, penta- or hexaethylene glycol and mixtures thereof. Preference is given to neopentyl glycol and/or cyclohexanedimethylol.

Suitable aminoalcohols are, for example, 2-aminoethanol, 2-(N-methylamino)ethanol, 3-aminopropanol, 4-aminobutanol, 1-ethylamino-butan-2-ol, 2-amino-2-methyl-1-propanol, 4-methyl-4-aminopen-tan-2-ol etc.

Suitable diamines are, for example, ethylenediamine, propylenediamine, 1,4-diaminobutane, 1,5-diaminopentane and 1,6-diamino-hexane, and α,ω-diamino polyethers which can be prepared by amination of polyalkylene oxides with ammonia.

Component b) is preferably a polymer having a number-average molecular weight in the range from about 300 to 5000, preferably from about 400 to 4000, in particular from 500 to 3000. Polymers b) which may be used are, for example, polyesterdiols, polyetherols and mixtures thereof. Polyetherols are preferably polyalkylene glycols, for example polyethylene glycols, polypropylene glycols, polytetrahydrofurans etc., block copolymers of ethylene oxide and propylene oxide or block copolymers of ethylene oxide, propylene oxide and butylene oxide which contain, in copolymerized form, the alkylene oxide units in random distribution or in the form of blocks. Component b) is preferably a polytetrahydrofuran, polyesterdiol or mixture thereof.

Suitable polytetrahydrofurans b) can be prepared by cationic polymerization of tetrahydrofuran in the presence of acidic catalysts, such as, for example, sulfuric acid or fluorosulfuric acid. Such preparation processes are known to the person skilled in the art.

Polyesterdiols b) which can be used preferably have a number-average molecular weight in the range from about 400 to 5000, preferably from 500 to 3000, in particular, from 600 to 2000.

Suitable polyesterdiols are all those which are normally employed to prepare polyurethanes, especially those based on aromatic dicarboxylic acids, such as terephthalic, isophthalic, phthalic, Na- or K-sulfoisophthalic acid, etc., on aliphatic dicarboxylic acids, such as adipic or succinic acid, etc., and on cycloaliphatic dicarboxylic acids, such as 1,2-, 1,3- or 1,4-cyclohexanedicarboxylic acid. Particularly suitable diols are aliphatic diols, such as ethylene glycol, propylene glycol, 1,6-hexanediol, neopentyl glycol, diethylene glycol, polyethylene glycols, polypropylene glycols, 1,4-dimethylolcyclohexane, and also poly(meth)-acrylatediols of the formula

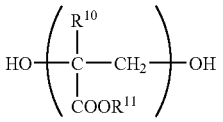

where $R^{10}$ is H or $CH_3$ and $R^{11}$ is $C_1$–$C_{18}$-alkyl (especially $C_1$–$C_{12}$- or $C_1$–$C_8$-alkyl) which have a molecular mass of up to about 3000. Diols of this kind can be prepared by conventional means and are obtainable commercially (Tegomer® grades MD, BD and OD from Gold-schmidt).

Preference is given to polyesterdiols based on aromatic and aliphatic dicarboxylic acids and aliphatic diols, especially those in which the aromatic dicarboxylic acid accounts for from 10 to 95 mol-%, in particular from 40 to 90 mol-% and, preferably, from 50 to 85 mol-% of the overall dicarboxylic acid component (the remainder being aliphatic dicarboxylic acids).

Particularly preferred polyesterdiols are the reaction products of phthalic acid/diethylene glycol, isophthalic acid/1,4-butanediol, isophthalic acid/adipic acid/1,6-hexanediol, 5-$NaSO_3$-isophthalic acid/phthalic acid/adipic acid/1,6-hexanediol, adipic acid/ethylene glycol, isophthalic acid/adipic acid/neopentyl glycol, isophthalic acid/adipic acid/neopentyl glycol/diethylene glycol/dimethylolcyclohexane, and 5-$NaSO_3$-isophthalic acid/isophthalic acid/adipic acid/neopentyl glycol/diethylene glycol/dimethylolcyclohexane.

Suitable compounds c), which contain two active hydrogen atoms and at least one ionogenic or ionic group per molecule, are, for example, compounds having carboxylate and/or sulfonate groups. Particular preference is given as component c) to dimethylolpropanoic acid and mixtures comprising it.

Suitable diamines and/or diols c) containing ionogenic or ionic groups are, for example, dimethylolpropanoic acid and compounds of the formula

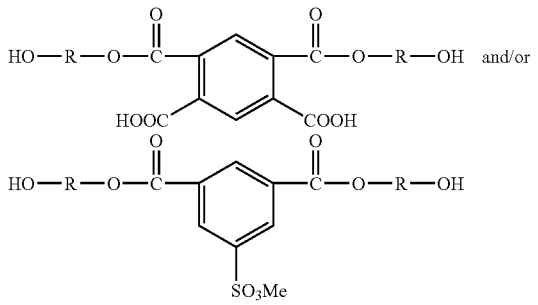

in which R is in each case a $C_2$–$C_{18}$-alkylene group, and Me is Na or K.

As component c) it is also possible to use compounds of the formula $$H_2N(CH_2)_n—NH—(CH_2)_m—COO^-M^+$$

$$H_2N(CH_2)_n—NH—(CH_2)_m—SO_3^-M^+$$

where m and n independently of one another are an integer from 1 to 8, in particular from 1 to 6, and M is Li, Na or K, and compounds of the formula $$H_2N(CH_2CH_2O)_p(CH_2CH(CH_3)O)_q(CH_2)_n—NH—(CH_2)_m—SO_3^-M^+$$

where m, n and M are as defined above, p and q independently of one another are an integer from 0 to 50, at least one of the two variables p or q being >0. The order of alkylene oxide units is arbitrary. The last-named compounds preferably have a number-average molecular weight in the range from about 400 to 3000.

If compounds having nitrogen-containing groups are used as component c), cationic polyurethanes are obtained. Components c) which can be used are, for example, compounds of the general formulae

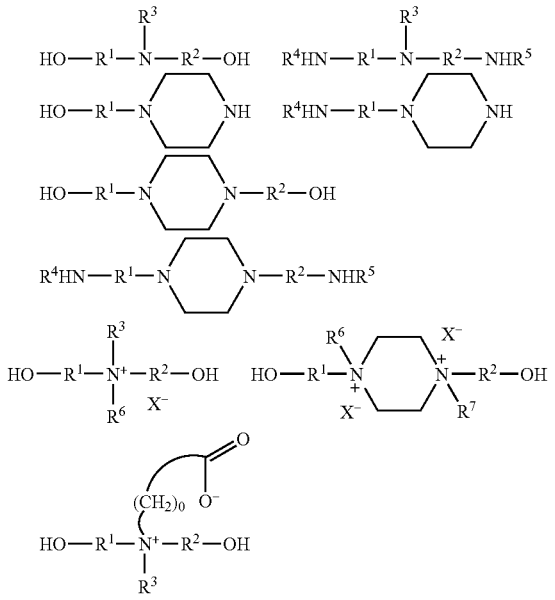

in which $R^1$ and $R^2$, which may be identical or different, are $C_2$–$C_8$-alkylene, $R^3$, $R^6$ and $R^7$, which may be identical or different, are $C_1$–$C_6$-alkyl, phenyl or phenyl-$C_1$–$C_4$-alkyl, $R^4$ and $R^5$, which may be identical or different, are H or $C_1$–$C_6$-alkyl, o is 1, 2 or 3, $X^-$ is chloride, bromide, iodide, $C_1$–$C_6$-alkylsulfate or $SO_4^{2-}/_2$. Particular preference is given to N-($C_1$- to $C_6$-alkyl)diethanolamines, such as methyldiethanolamine.

Suitable as component c) are also mixtures comprising at least one of the abovementioned anionic or anionogenic components and at least one of the abovementioned cationic or cationogenic components. Preference is then given to using mixtures comprising dimethylolpropanoic acid and N-methyldiethanolamine.

Component d) comprises customary aliphatic, cycloaliphatic and/or aromatic diisocyanates, such as tetramethylene diisocyanate, hexamethylene diisocyanate, methylenediphenyl diisocyanate, 2,4- and 2,6-tolylene diisocyanate and isomer mixtures thereof, o- and m-xylylene diisocyanate, 1,5-naphthylene diisocyanate, 1,4-cyclohexylene diisocyanate, dicyclohexylmethane diisocyanate and mixtures thereof, especially isophorone diisocyanate and/or dicyclohexylmethane diisocyanate. If desired, up to 3 mol % of these compounds may be replaced by triisocyanates.

The polyurethane prepolymers A) are prepared by reacting the compounds of components a), b) and, where appropriate, c) with component d). The temperature is in a range from about 60 to 140° C., preferably from about 70 to 100° C. The reaction can be carried out without solvent or in a suitable inert solvent or solvent mixture. Suitable solvents are aprotic polar solvents, e.g. tetrahydrofuran, ethyl acetate, N-methylpyrrolidone, dimethylformamide and, preferably, ketones, such as acetone and methyl ethyl ketone. The reaction is preferably carried out under an inert-gas atmosphere, for example under nitrogen. The components are used in amounts such that the ratio of NCO equivalent of the compounds of component d) to equivalent of active hydrogen atom of components a), b) and, where appropriate, c) is in a range from about 1.01:1 to 1.4:1, preferably from 1.03:1 to 1.3:1, in particular from 1.05:1 to 1.25:1. The resulting polyurethane prepolymers A) thus still have free isocyanate groups.

The polyurethane prepolymers preferably comprise, in copolymerized form, from 0.3 to 15% by weight, preferably from 0.5 to 12% by weight, of at least one component a), from 0.5 to 80% by weight, preferably from 1 to 65% by weight, of at least one component b), from 5 to 25% by weight, preferably from 8 to 20% by weight, of at least one component c), from 25 to 60% by weight, preferably from 35 to 53% by weight, of at least one component d).

The crosslinked, water-soluble or water-dispersible polyurethanes according to the invention are prepared by reacting at least one polyurethane prepolymer A), as described above, with at least one polymer B). The polymers B) comprise, in copolymerized form:

e) at least one α,β-ethylenically unsaturated monomer which additionally contains at least one group which is reactive toward isocyanate groups per molecule, f) optionally at least one α,β-ethylenically unsaturated monomer which is chosen from esters of α,β-ethylenically unsaturated mono- and/or dicarboxylic acids with $C_1$- to $C_{22}$-alkanols, amides of α,β-ethylenically unsaturated mono- and/or dicarboxylic acids with mono- and di-$C_1$- to $C_{22}$-alkylamines, esters of vinyl alcohol and allyl alcohol with $C_1$- to $C_{40}$-monocarboxylic acids, vinyl ethers, aromatic vinyl compounds, vinyl halides, vinylidene halides, $C_2$- to $C_8$-monoolefins, nonaromatic hydrocarbons having at least 2 conjugated double bonds and mixtures thereof, g) optionally at least one α,β-ethylenically unsaturated monomer which is chosen from N-vinylamides, N-vinyllactams, primary amides of α,β-ethylenically unsaturated monocarboxylic acids, vinyl- and allyl-substituted heteroaromatic compounds and mixtures thereof, h) optionally at least one further monomer containing a free-radically polymerizable, α,β-ethylenically unsaturated double bond and at least one ionogenic or ionic group per molecule.

Suitable monomers e) are the esters of α,β-ethylenically unsaturated mono- and dicarboxylic acids, such as acrylic acid, methacrylic acid, fumaric acid, maleic acid, itaconic acid and crotonic acid etc., with $C_1$–$C_{20}$-alkanediols. These include, for example, 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate etc. Preference is given to hydroxyethyl acrylate and hydroxyethyl methacrylate. Suitable monomers e) are also the esters of the abovementioned acids with triols and polyols, for example glycerol, erythritol, pentaerythritol and sorbitol etc.

Suitable monomers e) are also the esters and amides of the abovementioned α,β-ethylenically unsaturated mono- and dicarboxylic acids with $C_2$- to $C_{12}$-aminoalcohols which have a primary or secondary amino group. These include aminoalkyl acrylates and aminoalkyl methacrylates and the N-monoalkyl derivatives thereof which carry, for example, an N-$C_1$- to $C_8$-monoalkyl radical, such as aminomethyl acrylate, aminomethyl methacrylate, aminoethyl acrylate, aminoethyl methacrylate, N-methylaminomethyl acrylate, N-methylaminomethyl methacrylate, N-ethylaminomethyl acrylate, N-ethylaminomethyl methacrylate, N-(n-propyl) aminomethyl (meth)acrylate, N-isopropylaminomethyl (meth)acrylate and, preferably tert-butylaminoethyl acrylate and tert-butylaminoethyl methacrylate. These also include N-(hydroxy-$C_1$- to $C_{12}$-alkyl)(meth)acrylamides, such as N-hydroxymethyl(meth)acrylamide, N-hydroxyethyl (meth)-acrylamide etc.

Suitable monomers e) are also the amides of the abovementioned α,β-ethylenically unsaturated mono- and dicarboxylic acids with di- and polyamines which have at least two primary or two secondary or one primary and one secondary amino group. These include, for example, the corresponding amides of acrylic acid and methacrylic acid (referred to below by the syllable "(meth)"), such as aminomethyl(meth)acrylamide, aminoethyl(meth) acrylamide, aminopropyl(meth)acrylamide, amino-n-butyl (meth)acrylamide, methylaminoethyl(meth)acrylamide, ethylaminoethyl(meth)acryl-amide, methylaminopropyl (meth)acrylamide, ethylaminopropyl-(meth)acrylamide and methylamino-n-butyl(meth)acrylamide etc.

Suitable monomers f) are essentially hydrophobic, nonionic monomers. These include the esters of α,β-ethylenically unsaturated mono- and dicarboxylic acids with $C_1$–$C_{22}$-alkanols, preferably $C_1$–$C_{18}$-alkanols, e.g. the esters of acrylic acid and/or methacrylic acid with methanol, ethanol, n-propanol, isopropanol, n-buta-nol, sec-butanol, tert-butanol, n-pentanol, n-hexanol, n-heptanol, n-octanol, 2-ethylhexanol, dodecanol, hexadecanol and octadecanol etc.

Suitable monomers f) are also amides of α,β-ethylenically unsaturated mono- and dicarboxylic acids with mono- and dialkylamines which have from 1 to 22 carbon atoms, preferably from 1 to 18 carbon atoms, per alkyl radical. These include, for example, N-$C_1$- to $C_{22}$-alkyl(meth) acrylamides, such as N-methyl(meth)acrylamide, N-ethyl (meth) acrylamide, N-(n-propyl)(meth)acrylamide, N-isopropyl (meth)acrylamide, N-butyl(meth)acrylamide, N-(t-butyl) (meth)-acrylamide, N-pentyl(meth)acrylamide, N-hexyl (meth)acrylamide, N-heptyl(meth)acrylamide, N-octyl (meth)acrylamide, N-ethylhexyl(meth)acrylamide, N,N-dimethyl(meth)acrylamide and N,N-diethyl(meth) acrylamide etc.

Suitable monomers f) are also vinyl formate, vinyl acetate, vinyl propionate, vinyl-n-butyrate, vinyl stearate, vinyl laurate, styrene, α-methylstyrene, o-chlorostyrene, vinyltoluenes, vinyl chloride, vinylidene chloride, ethylene, propylene, butadiene, isoprene, chloroprene, methyl vinyl ether, ethyl vinyl ether, butyl vinyl ether, dodecyl vinyl ether etc.

Suitable monomers g) are essentially hydrophilic, nonionic monomers. These include, for example, N-vinylamides, such as N-vinylformamide, N-vinylacetamide, N-vinylpropionamide etc. Preference is given to N-vinylformamide.

Suitable monomers g) are also N-vinyllactams and derivatives thereof which may have, for example, one or more $C_1$–$C_6$-alkyl substituents, such as methyl, ethyl, n-propyl, isopropyl, n-butyl, sec-butyl, tert-butyl etc. These include, for example, N-vinyl pyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc.

Suitable monomers g) are also primary amides of the abovementioned and α,β-ethylenically unsaturated monocarboxylic acids, such as acrylamide, methacrylamide, ethacrylamide etc.

Suitable monomers g) are also vinyl- and allyl-substituted heteroaromatic compounds, such as 2- and 4-vinylpyridine, -allylpyridine, and preferably N-vinyl heteroaromatic compounds, such as N-vinylimidazole, N-vinyl-2-methylimidazole etc.

The compounds h) have at least one ionogenic or ionic group per molecule, which is preferably chosen from carboxylate groups and/or sulfonate groups and the salts thereof obtainable by partial or complete neutralization with a base, and also tertiary amine groups, which may be partially or completely protonated and quaternized. Suitable bases for the neutralization or acids for the protonation and alkylating agents for the quaternization are the polyurethanes given below after the preparation of the polyurethanes according to the invention.

Suitable monomers h) are, for example, the aforementioned α,β-ethylenically unsaturated mono- and/or dicarboxylic acids and their half-esters and anhydrides, such as acrylic acid, methacrylic acid, fumaric acid, maleic acid, itaconic acid, crotonic acid, maleic anhydride, monobutyl maleate etc. Preference is given to acrylic acid, methacrylic acid and alkali metal salts thereof, such as sodium and potassium salts thereof.

Suitable monomers h) are also acrylamidoalkanesulfonic acids and salts thereof, such as 2-acrylamido-2-methylpropanesulfonic acid and alkali metal salts thereof, e.g. sodium and potassium salts thereof.

Other suitable compounds h) are the esters of the abovementioned α,β-ethylenically unsaturated mono- and dicarboxylic acids with $C_2$- to $C_{12}$-aminoalcohols which are $C_1$- to $C_8$-dialkylated in the amine nitrogen. These include, for example, N,N-dimethylaminomethyl (meth)acrylate, N,N-dimethylaminoethyl (meth)acrylate, N,N-diethylaminoethyl (meth)acrylate, N,N-dimethylaminopropyl (meth)acrylate, N,N-diethylaminopropyl (meth)acrylate etc. Preference is given to N,N-dimethylaminopropyl acrylate and N,N-dimethylaminopropyl (meth)acrylate.

Suitable monomers h) are also the amides of the abovementioned α,β-ethylenically unsaturated mono- and dicarboxylic acids with diamines which have a tertiary and a primary or secondary amino group. These include, for example, N-[2-(dimethylamino)ethyl]-acrylamide, N-[2-(dimethylamino)ethyl]methacrylamide, N-[3-(dimethylamino)propyl]acrylamide, N-[3-(dimethylamino) propyl]methacrylamide, N-[4-(dimethylamino)butyl] acrylamide, N-[4-(dimethylamino)-butyl]methacrylamide, N-[2-(diethylamino)ethyl]acrylamide etc.

The polymer B) preferably comprises, in copolymerized form, in addition to component e), at least one component f) and/or g) and, where appropriate, a component h).

Polymer B) preferably comprises, in copolymerized form, from 0.05 to 15% by weight, preferably from 0.1 to 10% by weight, of at least one component e), from 0 to 99.9% by weight of at least one component f), from 0 to 99.9% by weight of at least one component g), and from 0 to 50% by weight, preferably from 0.1 to 46% by weight, of at least one component h).

The total amount of components f) and g) is preferably in a range from 30 to 99.9% by weight, in particular from 40 to 99.5% by weight, especially from 50 to 99.5% by weight.

In a preferred embodiment, the polymer B) comprises, in copolymerized form, from 0.1 to 10% by weight, preferably from 0.5 to 5% by weight, of at least one component e)

from 50 to 99.9% by weight, preferably from 60 to 99.5% by weight, of at least one component g), and from 0 to 40% by weight, preferably from 0 to 35% by weight, of at least one component h).

In another preferred embodiment, the polymer B) comprises, in copolymerized form, from 0.1 to 10% by weight, preferably from 0.5 to 5% by weight, of at least one component e), from 50 to 99.9% by weight, preferably from 60 to 90% by weight, of at least one component f), and from 0 to 50% by weight, preferably from 10 to 46% by weight, of at least one component h).

In another preferred embodiment, the polymer B) comprises, in copolymerized polymerized form, from 0.1 to 10% by weight, preferably from 0.5 to 5% by weight, of at least one component e), from 0.1 to 99.9% by weight, preferably from 0.1 to 90% by weight, of at least one component f), from 0.1 to 99.9% by weight, preferably from 0.1 to 99.5% by weight, of at least one component g), and from 0 to 50% by weight, preferably from 0 to 46% by weight, of at least one component h).

The invention further provides a polymer B) which comprises, in copolymerized form, from 0.05 to 15% by weight, preferably from 0.1 to 10% by weight, of a component e), as defined in claim 5, preferably tert-butylaminoethyl acrylate and/or tert-butylaminoethyl methacrylate, from 0 to 99.9% by weight of at least one component f), from 0.1 to 99.9% by weight of at least one component g), from 0 to 50% by weight, preferably from 0.1 to 46% by weight, of at least one component h)

where the total amount of components f) and g) is preferably in a range from 30 to 99.9% by weight.

The polymer B) is prepared by customary processes known to the person skilled in the art. These include bulk polymerization and, preferably, solution polymerization. The polymerization temperature is usually from 30 to 120° C., preferably from 40 to 100° C. The polymerization medium can consist either only of an organic solvent or of mixtures of water and at least one water-miscible, organic solvent. Preferred organic solvents are, for example, alcohols, such as methanol, ethanol, n-propanol, isopropanol, n-butanol, ketones, such as acetone and methyl ethyl ketone, tetrahydrofuran etc. Solution polymerization can either be carried out as a batch process or else in the form of a feed ethod, including monomer feed, stepwise and gradient procedure. Preference is generally given to the feed method in which, where appropriate, some of the polymerization batch is heated to the polymerization temperature and then the remainder of the polymerization batch is fed to the polymerization zones, usually via one or also two or more, spatially separated feed lines, continuously, stepwise or with superimposition of a concentration gradient with maintenance of the polymerization.

Suitable initiators for the free-radical polymerization are azo compounds suitable for the free-radical polymerization. These include aliphatic or cycloaliphatic azo compounds, e.g. 2,2'-azobis(isobutyronitrile), 2,2'-azobis(2-methylbutyronitrile), 2,2'-azobis(2,4-dimethylvaleronitrile), 1,1'-azobis(1-cycloheanecarbonitrile), 2-(carbamoylazo) isobutyronitrile, 4,4'-azobis(4-cyanovaleric acid) and alkali metal and ammonium salts thereof, for example the sodium salt, dimethyl-2,2'-azobisisobutyrate, 2,2'-azobis[2-(2-imidazolin-2-yl)propane], 2,2'-azobis(2-amidinopropane) and the acid addition salts of the last two compounds, e.g. the dihydrochlorides.

Other suitable initiators are hydrogen peroxide, hydroperoxides in combination with reducing agents and per salts. Suitable hydroperoxides are, for example, t-butyl hydroperoxide, t-amyl hydroperoxide, cumene hydroperoxide and pinane hydroperoxide, each in combination with, for example, a salt of hydroxymethanesulfinic acid, an iron(II) salt or ascorbic acid. Suitable per salts are, in particular, alkali metal peroxydisulfates.

The amount of initiator used, based on the monomers, is generally in a range from about 0.02 to 15 mol %, preferably 0.05 to 3 mol %.

If relatively low molecular weights are desired, these can be set by adding a regulator to the polymerization batch. Suitable regulators are, for example, aldehydes, such as formaldehyde, acetaldehyde, propionaldehyde, n-butyraldehyde and isobutyraldehyde, formic acid, ammonium formate, hydroxylammonium sulfate and hydroxylammonium phosphate. Other possible regulators may contain sulfur in organically bonded form, such as di-n-butyl sulfide, di-n-octyl sulfide, diphenyl sulfide, etc., or regulators comprising sulfur in the form of SH groups, such as n-butyl mercaptan, n-hexyl mercaptan or n-dodecyl mercaptan. Suitable compounds are also water-soluble, sulfur-containing polymerization regulators, for example hydrogen sulfites and disulfites. Further suitable regulators are allyl compounds, such as allyl alcohol or allyl bromide, benzyl compounds, such as benzyl chloride or alkyl halides, such as chloroform or tetrachloromethane.

If desired, one or more polymerization initiators are added to the polymer solution following the polymerization reaction, and the polymer solution is heated, for example to the polymerization temperature or to temperatures above the polymerization temperature, in order to complete the polymerization. Suitable compounds are the azo initiators given above, and also all other customary initiators suitable for free-radical polymerization in aqueous solution, for example, peroxides, hydroperoxides, peroxodisulfates, percarbonates, peroxo esters and hydrogen peroxide. As a result, the polymerization reaction achieves a higher conversion, for example of 99.9%. The solutions which form during the polymerization can, where appropriate, be converted into solid powders by a prior art drying process. Preferred processes are, for example, spray-drying, spray fluidized-bed drying, roller-drying and belt-drying. Freeze-drying and freeze concentration can also be used. If desired, some or all of the solvent can be removed by customary methods, e.g. distillation at reduced pressure, and, here appropriate, be replaced by the solvent used for the subsequent reaction of polymer B) with the polyurethane prepolymer A). Hydroxyl-containing polymers B), which have been prepared in a solvent having active hydrogen atoms, are preferably dried prior to reaction with A), and then used in a solvent or solvent mixture which does not have any active hydrogen atoms.

The polyurethanes according to the invention are prepared by reacting the polyurethane prepolymer A) with the polymer B). The ratio of NCO equivalent of component A) to equivalent active hydrogen atom of component B) is generally in a range from about 20:1 to 1:1, preferably from 10:1 to 1:1, in particular from 10:1 to 1.01:1. The temperature of the reaction is generally in a range from about 10 to 150° C., preferably from about 20 to 90° C. The reaction can advantageously be carried out in a suitable inert solvent or solvent mixture. Suitable solvents are those specified above for the preparation of the polyurethane prepolymers A). If component B) is a hydroxyl-containing polymer, then the reaction temperature is preferably in a range from about 60 to 150° C. The reaction is then preferably carried out a solvent or solvent mixture which does not have any active hydrogen atoms. Preference is given to ketones, such as acetone, methyl ethyl ketone and mixtures thereof. If component B) is a polymer having largely or exclusively primary and/or secondary amino groups as groups which are reactive towards isocyanate groups, then the reaction temperature is preferably in a range from about 20 to 80° C. The reaction can then, if desired, be carried out in a solvent or solvent mixture which may have active hydrogen atoms. In addition to the substances mentioned above, preference is given to using alcohols, such as methanol and ethanol, mixtures of alcohols and water and also mixtures of alcohols and the abovementioned ketones. The polyurethanes according to the invention are preferably prepared by introducing initially a solution of one of the components A) or B) into a customary reactor known to the person skilled in the art, e.g. a stirred reactor. The second component is then preferably likewise added in the form of a solution, and when addition is complete, the reaction is continued until the NCO content of the mixture remains constant. If the resulting polyurethanes still have free isocyanate groups, the latter are finally inactivated by adding amines, preferably aminoalcohols. Suitable aminoalcohols are those described above, preferably 2-amino-2-methyl-1-propanol.

The polyurethanes containing acid groups can be neutralized partially or completely using a base.

As a rule, the resulting salts of the polyurethanes have better solubility in water or dispersibility in water than the unneutralized polyurethanes. Suitable bases for the neutralization of the polyurethanes are alkali metal bases, such as sodium hydroxide solution, potassium hydroxide solution, soda, sodium hydrogencarbonate, potassium carbonate or potassium hydrogencarbonate and alkaline earth metal bases, such as calcium hydroxide, calcium oxide, magnesium hydroxide or magnesium carbonate, and ammonia and amines. Suitable amines are, for example $C_1$–$C_6$-alkylamines, preferably n-propylamine and n-butylamine, dialkylamines, preferably diethylpropylamine and dipropylmethylamine, trialkylamines, preferably triethylamine and triisopropylamine, $C_1$–$C_6$-alkyldiethanolamines, preferably methyl- or ethyldiethanolamine and di-$C_1$–$C_6$-alkylethanolamines. Particularly for use in hair treatment compositions, 2-amino-2-methyl-1-propanol, diethylaminopropylamine and triisopropanolamine have proven successful for the neutralization of the acid-containing polyurethanes. If desired, it is also possible to use a siloxane-containing amine for the neutralization, preferably a monoamine, e.g. 3-aminopropyltrimethoxysilane. Neutralization of the acid-containing polyurethanes can also be carried out using mixtures of two or more bases, e.g. mixtures of sodium hydroxide solution and triisopropanolamine. Depending on the intended use, neutralization can be partial, e.g. up to 20 to 40%, or complete, i.e. up to 100%.

The polyurethanes containing amino groups or protonated or quaternized amino groups are, because of their cationic groups, generally readily soluble in water or water/alcohol mixtures, or at least dispersible without the aid of emulsifiers. Charged cationic groups can be produced from the present tertiary amine nitrogens either by protonation, e.g. using carboxylic acids, such as lactic acid, or mineral acids, such as phosphoric acid, sulfuric acid and hydrochloric acid, or by quaternization, e.g. using alkylating agents, such as $C_1$- to $C_4$-alkyl halides or sulfates. Examples of such alkylating agents are ethyl chloride, ethyl bromide, methyl chloride, methyl bromide, dimethyl sulfate and diethyl sulfate.

In a suitable embodiment, the polyurethanes according to the invention can have both acid groups and amino groups. The difference in the number of acid groups and the number of amino groups ($|\Delta SZ\text{-}AZ|$) is preferably in a range from about 15 to 150, preferably from 30 to 100. Acid number and amine number are in each case defined as mg of KOH/g of test substance.

If, in the preparation of the polyurethanes, a water-miscible organic solvent is used, the latter can be subsequently removed by customary processes known to the person skilled in the art, e.g. by distillation at reduced pressure. Prior to removal of the solvent, water can additionally be added to the polyurethane. Replacement of the solvent by water gives a solution or dispersion of the polymer, from which, if desired, the polymer can be obtained in the usual manner, e.g. by spray-drying.

The polyurethanes according to the invention do not have any siloxane groups. Their K values (measured in accordance with E. Fikentscher, Cellulose-Chemie 13 (1932), p. 58–64, on a 1% strength solution in N-methylpyrrolidone) are generally in a range from about 15 to 90, preferably from 20 to 60. Their glass transition temperature is generally at least 0° C., preferably at least 20°C., particularly preferably at least 25° C. and especially at least 30° C. If the polyurethanes according to the invention have two or more glass transition temperatures, then at least one of them is in the stated range. The other(s) is/are then preferably below the temperature range given above.

The polyurethanes according to the invention can be used as auxiliaries in cosmetics and pharmacy, in particular as or in coating composition(s) for keratinous surfaces (hair, skin and nails) and as coating compositions and/or binders for solid medicaments. In addition, they can be used as or in coating composition(s) for the textile, paper, printing, leather and adhesives industries.

In particular, they can be used in hair cosmetics. The abovementioned polyurethanes can also be used in creams and as tablet coatings and tablet binders. They are also suitable as binders and adhesives for cosmetic products, e.g. in the preparation of stick-shaped cosmetic products, such as deodorant sticks, and makeup sticks etc.

The present invention also provides a cosmetic or pharmaceutical composition which comprises the polyurethanes according to the invention. The composition generally comprises the polyurethanes in an amount in the range from 0.2 to 30% by weight, based on the overall weight of the composition.

The cosmetic compositions according to the invention are particularly suitable as compositions for coating keratinous surfaces (hair, skin and nails). The compounds employed therein are water-soluble or water-dispersible. Where the compounds employed in the compositions according to the invention are dispersible in water, they can be applied in the form of aqueous microdispersions having particle diameters of usually from 1 to 250 nm, preferably from 1 to 500 nm. In this case the solids contents of the preparations are usually within a range from about 0.5 to 20% by weight, preferably from 1 to 12% by weight. In general, such microdispersions do not require stabilization by emulsifiers or surfactants.

With preference, the compositions according to the invention can be in the form of a hair treatment composition, especially in the form of a hairspray. For use as hairsetting agents, preferred compositions are those comprising polyurethanes whose glass transition temperature Tg is at least >20° C., preferably >30° C. The K value of these polymers is preferably in a range from 23 to 90, in particular from 25 to 60.

The compositions are preferably hair treatment compositions, and are usually in the form of an aqueous dispersion or in the form of an alcoholic or aqueous-alcoholic solution. Examples of suitable alcohols are ethanol, propanol, isopropanol, etc.

In addition, the hair treatment compositions according to the invention generally comprise customary cosmetic auxiliaries, examples being softeners, such as glycerol and glycol; emollients; perfumes; UV absorbers; colorants; antistatics; combability improvers; preservatives; and antifoams.

When formulated as hairsprays, the novel compositions comprise a sufficient amount of a propellant: for example, a low-boiling hydrocarbon or ether, such as propane, butane, isobutane or dimethyl ether. As propellants it is also possible to use compressed gases, such as nitrogen, air or carbon dioxide. The amount of propellant can be kept low so as not unnecessarily to raise the VOC content. In general the said amount is not more than 55% by weight, based on the overall weight of the composition. However, higher VOC contents of 85% by weight or more are also possible if desired.

The polyurethanes described above can also be employed in the compositions in combination with other hair polymers. Such polymers are, in particular:

nonionic, water-soluble or water-dispersible polymers or oligomers, such as polyvinylcaprolactam, e.g. Luviskol Plus (BASF), or polyvinylpyrrolidone and its copolymers, especially with vinyl esters such as vinyl acetate, e.g. Luviskol VA 37 (BASF); polyamides, for example those based on itaconic acid and aliphatic diamines;

amphoteric or zwitterionic polymers, such as the octylacrylamide/methyl methacrylate/tert-butylamionoethyl methacrylate/2-hydroxypropyl methacrylate copolymers obtainable under the names Amphomer® (Delft National), and zwitterionic polymers as disclosed, for example, in German Patent Applications DE 39 29 973, DE 21 50 557, DE 28 17 369 and DE 37 08 451. Acrylamidopropyltrimethylammonium chloride/acrylic acid and/or methacrylic acid copolymers, and the alkali metal salts and ammonium salts thereof, are preferred zwitterionic polymers. Suitable zwitterionic polymers are also methacryloylethyl betaine/methacrylate copolymers, which are commercially available under the name Amersette® (AMERCHOL) and copolymers of hydroxyethyl methacrylate, methyl methacrylate, N,N-dimethylaminoethyl methacrylate and acrylic acid (Jordapon®);

anionic polymers, such as vinyl acetate/crotonic acid copolymers, as are commercially available, for example, under the names Resyn® (NATIONAL STARCH), Luviset® (BASF) and Gafset® (GAF), vinylpyrrolidone/vinyl acrylate copolymers, obtainable for example under the trademark Luviflex® (BASF). A preferred polymer is the vinylpyrrolidone/acrylate terpolymer obtainable under the name Luviflex® VBM-35 (BASF), acrylic acid/ethyl acrylate/N-tert-butylacrylamide terpolymers, which are marketed, for example, under the name Ultrahold® strong (BASF), and Luvimer® (BASF, terpolymer of t-butyl acrylate, ethyl acrylate and methacrylic acid), or cationic (quaternized) polymers, e.g. cationic polyacrylate copolymers based on N-vinyllactams and derivatives thereof (N-vinylpyrrolidone, N-vinylcaprolactam etc.) and also customary cationic hair conditioner polymers, e.g. Luviquate (copolymer of vinylpyrrolidone and vinylimidazolium methochloride), Luviquat® Hold (copolymer of quaternized N-vinylimidazole, N-vinylpyrrolidone and N-vinylcaprolactam), Merquat® (polymer based on dimethyldiallylammonium chloride), Gafquat® (quaternary polymers formed by reacting polyvinylpyrrolidone with quaternary ammonium compounds), polymer JR (hydroxyethylcellulose with cationic groups), polyquaternium types (CTFA names) etc.;

nonionic, siloxane-containing, water-soluble or -dispersible polymers, e.g. polyether siloxanes, such as Tegopren® (Gold-schmidt) or Belsil® (Wacker).

The crosslinked polyurethanes according to the invention can be employed as a mixture with another amido-functional hair polymer. Such polymers include, for example, the polyurethanes described in DE-A-42 25 045, the above-described vinylpyrrolidone/acrylate terpolymers and acrylic acid/ethyl acrylate/N-tert-butylacrylamide terpolymers (e.g. Ultrahold® strong from BASF AG), the above-described amido-functional amphoteric polymers (e.g. Amphomere®) and, in particular, copolymers having a content of amido-functional monomers, such as N-vinyllactams, of at least 30% by weight (e.g. Luviskol®plus and Luviskol®VA37 from BASF AG).

The crosslinked polyurethanes according to the invention can also be used as a mixture with another siloxane-containing hair polymer, preferably siloxane-containing polyurethanes.

The other hair polymers are preferably present in amounts of up to 10% by weight, based on the overall weight of the composition.

A preferred hair treatment composition comprises:

a) from 0.5 to 20% by weight of at least one water-soluble or -dispersible polyurethane according to the invention, b) from 40 to 99% by weight, preferably from 50 to 98% by weight, of a solvent chosen from water and water-miscible solvents, preferably $C_2$- to $C_5$ alcohols, in particular ethanol, and mixtures thereof, c) from 0 to 50% by weight of a propellant, preferably dimethyl ether, d) from 0 to 15% by weight of at least one water-soluble or -dispersible hair polymer which is different from a), e) from 0 to 0.2% by weight of at least one water-insoluble silicone, f) from 0 to 2% by weight of at least one nonionic, siloxanecontaining, water-soluble or -dispersible polymer and customary additives.

The composition according to the invention may comprise, as component d), at least one other hair polymer which is dispersible or soluble in water. The proportion of this component will then in general be from about 0.1 to 15% by weight, preferably from 0.1 to 10% by weight, based on the overall weight of the composition. In this context it is possible with preference to employ water-soluble or water-dispersible polyurethanes which contain siloxane groups in copolymerized form.

The composition according to the invention may comprise, as component e), at least one water-insoluble silicone, especially a polydimethylsiloxane, e.g. the Abile grades from Goldschmidt. The proportion of this component will then in general be from about 0.0001 to 0.2% by weight, preferably from 0.001 to 0.1% by weight, based on the overall weight of the composition.

The composition according to the invention may comprise, as component f), at least one nonionic, siloxane-containing, water-soluble or -dispersible polymer, chosen in particular from the polyether siloxanes described above. The proportion of this component will then in general be from about 0.001 to 2% by weight, based on the overall weight of the composition.

The composition according to the invention may additionally comprise, if desired, an antifoam based, for example, on silicone. The amount of the antifoam will then in general be up to about 0.001% per weight, based on the overall amount of the composition.

The compositions according to the invention have the advantage that on the one hand they give the hair the desired set and on the other hand the polymers are easy to wash out (redispersible). Furthermore, it is possible to formulate hair treatment compositions with a VOC content of less than 85% by weight, preferably less than 60% by weight, and also to prepare purely aqueous formulations, even if they are formulated as hairsprays.

The invention is illustrated further by the following non-limiting examples.

EXAMPLES

Examples 1 to 4

Polyurethane Prepolymer Preparation

In a stirred apparatus fitted with stirrer, dropping funnel, thermometer, reflux condenser and equipment for operating under nitrogen, a polyesterdiol (Mn=1000 g/mol, prepared from isophthalic acid, adipic acid and hexanediol) (Examples 1 to 3) and/or a polytetrahydrofuran (Mn=1000 g/mol) (Examples 3, 4), cyclohexanedimethylol (Example 1) or neopentyl glycol (Examples 2 to 4), dimethylolpropanoic acid and, where appropriate, methyldiethanolamine (Example 4) in an amount in accordance with Table 1 were dissolved in methyl ethyl ketone (solids content of the resulting reaction solution about 75%) with heating to a temperature of about 70° C. and with stirring. Isophorone diisocyanate was then added dropwise with stirring in an amount in accordance with Table 1, during which the reaction temperature increased. At an internal temperature of 85° C., the reaction mixture was then stirred until the isocyanate content of the mixture remained virtually constant (from about 0.5 to 1%). The reaction mixture was diluted to 40% by weight with methyl ethyl ketone and cooled to room temperature with stirring.

TABLE 1

| Ex. No. | Polyesterdiol[1] [mol] | Poly(THF)[2] [mol] | CHDM[3] [mol] | NPG[4] [mol] | DMPE[5] [mol] | MDEA[6] [mol] | IPDI[7] [mol] |
|---|---|---|---|---|---|---|---|
| 1 | 0.8 | — | 1.7 | — | 3 | — | 6 |
| 2 | 1.2 | — | — | 1.4 | 3 | — | 6 |
| 3 | 0.7 | 0.7 | — | 1.2 | 3 | — | 6 |
| 4 | — | 1 | — | 1.0 | 3 | 0.5 | 6 |

[1]Polyesterdiol of isophthalic acid, adipic acid, hexanediol, $M_n$ = 1000 g/mol
[2]Polytetrahydrofuran, $M_n$ = 1000 g/mol
[3]CHDM = Cyclohexanedimethylol
[4]NPG = Neopentyl glycol
[5]DMPA = Dimethylolpropanoic acid
[6]MDEA = N-Methyldiethanolamine
[7]IPDI = Isophorone diisocyanate

Examples 5 to 21

Preparation of Polymer B)

| Preparation of Polymer B) | | |
|---|---|---|
| Feed 1: | 300 g | monomer mixture according to Table 2 |
| | 30 g | solvent: Examples 5, 6, 8-13, 17-21: ethanol; Examples 7, 14-16: ethanol/water (1:1) |
| Feed 2: | 0.6 g | 2,2'-azobis(2-methylbutyronitrile) |
| | 150 g | ethanol |
| Feed 3: | 3.0 g | 2,2'-azobis(2-methylbutyronitrile) |
| | 150 g | ethanol |

In a stirred apparatus fitted with reflux condenser and two separate feed devices 20% by weight of feed 1 (monomer mixture in accordance with Table 2), 12% by weight of feed 2 and 120 g of ethanol were heated to about 75° C. After partial polymerization, detectable when the viscosity starts to increase, the remainder of feed 1 was added over the course of 4 hours and the remainder of feed 2 over the course of 5 hours, the internal temperature being maintained at from about 70 to 75° C. Feed 3 was then added over the course of 2 hours, the internal temperature being increased to about 80° C. When addition was complete, the mixture was after polymerized for about another 5 hours at this temperature. The resulting polymers can be used for the polyurethane preparation without further measures for reducing the residual monomer content. Polymers with very low residual monomer contents are obtained if, instead of feed 3,2,5-bis-(tert-butylperoxy-2,5-dimethylhexane) (Trigonox® 101 from Akzo Nobel) in 150 g of ethanol, for example, is added to the reaction mixture over the course of 2 hours, and then the mixture is after polymerized for about another 5 hours at a temperature of about 130° C. under the autogenous pressure of the reaction mixture.

Following the polymerization, the hydroxyl-containing polymers of Examples 5 to 8 are dried by spray drying, and then 40% by weight strength solutions of these polymers in methyl ethyl ketone are prepared for the subsequent reaction.

In the case of the polymers of Examples 14 to 16 prepared in a solvent mixture of ethanol/water (1:1), the solvent is removed by distillation under reduced pressure at about 40° C., and then 40% by weight strength solutions in ethanol are prepared for the subsequent reaction.

The ethanolic solutions of the other polymers are likewise adjusted to 40% by weight by adding further ethanol.

TABLE 2

| | Monomer feed 1 | | | | | | | | |
|---|---|---|---|---|---|---|---|---|---|
| Ex. No. | VP[1] [% by wt.] | VCap[2] [% by wt.] | t-BA[3] [% by wt.] | EHMA[4] [% by wt.] | HEMA[5] [% by wt.] | t-BAEMA[6] [% by wt.] | MAS[7] [% by wt.] | AMPS-Na[8] [% by wt.] | DMAPMA[9] [% by wt.] |
| 5 | 97 | — | — | — | 3 | — | — | — | — |
| 6 | 47 | 50 | — | — | 3 | — | — | — | — |
| 7 | 37 | — | 45 | — | 3 | — | MAS-Na[10] 15 | — | — |
| 8 | 47 | 42 | — | — | 3 | — | — | — | 8 |
| 9 | 98 | — | — | — | — | 2 | — | — | — |
| 10 | — | 99.5 | — | — | — | 0.5 | — | — | — |
| 11 | — | 69 | 30 | — | — | 1 | — | — | — |
| 12 | 69 | — | 30 | — | — | 1 | — | — | — |
| 13 | 59 | — | 35 | 5 | — | 1 | — | — | — |
| 14 | — | — | 73 | — | — | 2 | 25 | — | — |
| 15 | — | — | 23 | 30 | — | 2 | — | 45 | — |
| 16 | 74 | — | — | — | — | 1 | — | 25 | — |
| 17 | 90 | — | — | — | — | 1 | — | — | 9 |
| 18 | 45 | 45 | — | — | — | 1 | — | — | 9 |
| 19 | — | 90 | — | — | — | 1 | — | — | 9 |
| 20 | — | 90.5 | — | — | — | 0.5 | — | — | 9 |
| 21 | 45 | — | 35 | 5 | — | 1 | — | — | 14 |

[1]VP = Vinylpyrrolidone
[2]VCap = Vinylcaprolactam
[3]t-BA = tert-Butyl acrylate
[4]EHMA = Ethylhexyl methacrylate
[5]HEMA = Hydroxyethyl methacrylate
[6]t-BAEMA = tert-Butylaminoethyl methacrylate
[7]MAS = Methylacrylic acid
[8]AMPS-Na = Sodium salt of acrylamidomethylpropanesulfonic acid
[9]DMAPMA = Dimethylaminopropyl methacrylate
[10]MAS-Na = Sodium salt of methyacrylic acid

Examples 22 to 26

Polyurethane Preparation

In a stirred apparatus fitted with stirrer, dropping funnel, thermometer and reflux condenser a 40% strength by weight solution of a polyurethane polymer from Example 1 to 3 in methyl ethyl ketone, as given in Table 3, was heated to 60° C. A 40% by weight strength solution of a hydroxyl-containing polymer B) from Example 5 to 8, likewise in methyl ethyl ketone, in accordance with Table 3 was then mixed in. The reaction mixture was stirred at a temperature of about 85° C. until the isocyanate group content of the mixture remained virtually constant (about 2 hours). Water was then added to the reaction mixture, and the reaction product was neutralized using 2-amino-2-methylpropanol (pH about 8.0). The methyl ethyl ketone was then distilled off under reduced pressure at 40° C., and an aqueous dispersion of the polyurethane was obtained.

A pulverulent product can be obtained by spray-drying.

Examples 27 to 41

A stirred apparatus fitted with stirrer, dropping funnel, thermometer and reflux condenser was charged with a 40% by weight strength solution of a polyurethane prepolymer from Example 1 to 4 in methyl ethyl ketone in accordance with Table 3. At a temperature of about 30° C., a polymer B) in accordance with Table 3 in the form of a 40% by weight strength solution in ethanol was then mixed in. The reaction mixture was then stirred for about 1 hour at the ambient temperature. Water was then added to the reaction mixture, and the reaction product was neutralized using 2-amino-2-methylpropanol (pH about 8.0). The methyl ethyl ketone was then distilled off under reduced pressure at 40° C., and an aqueous dispersion of the polyurethane was obtained.

A pulverulent product can be obtained by spray-drying.

TABLE 3

| | PU prepolymer | | Polymer B) | | |
|---|---|---|---|---|---|
| Ex. No. | Ex. No. | [% by weight] | Ex. No. | [% by weight] | K value[1] |
| 22 | 1 | 80 | 5 | 20 | 33 |
| 23 | 1 | 50 | 6 | 50 | 37.3 |
| 24 | 1 | 90 | 8 | 10 | 32.4 |
| 25 | 2 | 90 | 8 | 10 | 34.7 |
| 26 | 3 | 90 | 8 | 10 | 36.1 |
| 27 | 1 | 90 | 9 | 10 | 34.7 |
| 28 | 1 | 70 | 10 | 30 | 35.4 |
| 29 | 1 | 90 | 14 | 10 | 37.6 |
| 30 | 1 | 80 | 16 | 20 | 39.4 |
| 31 | 1 | 80 | 18 | 20 | 31.2 |
| 32 | 2 | 80 | 18 | 20 | 32 |
| 33 | 3 | 80 | 18 | 20 | 35.3 |
| 34 | 1 | 90 | 21 | 10 | 32.1 |
| 35 | 1 | 80 | 21 | 20 | 37.4 |
| 36 | 1 | 20 | 21 | 80 | 45.2 |
| 37 | 3 | 50 | 10 | 50 | 42 |

TABLE 3-continued

| | PU prepolymer | | Polymer B) | | |
|---|---|---|---|---|---|
| Ex. No. | Ex. No. | [% by weight] | Ex. No. | [% by weight] | K value[1)] |
| 38 | 4 | 50 | 10 | 50 | 38.7 |
| 39 | 4 | 90 | 10 | 10 | 32.1 |
| 40 | 4 | 90 | 18 | 10 | 33.2 |
| 41 | 4 | 10 | 14 | 90 | 42.8 |

[1)]1% by weight strenght solution in N-methylpyrrolidone

The abovedescribed aqueous dispersions of the crosslinked polyrethanes according to the invention can be used directly for the preparation of hairspray formulations.

APPLICATION EXAMPLES

Examples 42 to 61

Aerosol hairspray formulations with a VOC content of 97% by weight:

| | |
|---|---|
| Polyurethane in accordance with Example 22-41 | 3.00% by weight |
| Ethanol | 62.00% by weight |
| Dimethyl ether | 34.96% by weight |
| Perfume, additives | q.s. |

Examples 62 to 76

Compact aerosol hairspray formulations with a VOC content of 90% by weight:

| | |
|---|---|
| Polyurethane in accordance with Example 22-36 | 10.00% by weight |
| Ethanol | 55.00% by weight |
| Dimethyl ether | 34.96% by weight |
| Perfume, additives | q.s. |

Examples 77 to 96

Hairspray formulations with a VOC content of 80% by weight:

| | |
|---|---|
| Polyurethane in accordance with Example 22-41 | 5.00% by weight |
| Ethanol | 45.00% by weight |
| Water | 15.00% by weight |
| Dimethyl ether | 34.96% by weight |
| Perfume, additives | q.s. |

Examples 97 to 116

Hairspray formulations with a VOC content of 55% by weight:

| | |
|---|---|
| Polyurethane in accordance with Example 22-41 | 5.00% by weight |
| Ethanol | 20.00% by weight |
| Water | 40.00% by weight |
| Dimethyl ether | 34.96% by weight |
| Perfume, additives | q.s. |

Examples 117 to 136

Pump hairspray formulations with 0 VOC content:

| | |
|---|---|
| Polyurethane in accordance with Example 22-41 | 10.00% by weight |
| Water | 89.97% by weight |
| Perfume, additives | q.s. |

We claim:

1. A cosmetic or pharmaceutical composition which comprises at least one crosslinked, water-soluble or water-dispersible polyurethane of A) at least one water-soluble or water-dispersible polyurethane prepolymer containing terminal isocyanate groups of a) at least one compound having a molecular weight in the range from 56 to 300 which contains two active hydrogen atoms per molecule, b) at least one polymer containing two active hydrogen atoms per molecule, c) at least one compound which contains two active hydrogen atoms and at least one ionogenic or ionic group per molecule, d) at least one diisocyanate, B) at least one polymer containing groups which are reactive toward isocyanate groups, [chosen] *selected* from hydroxyl, [and primary and] secondary amino and[/or] carboxyl groups, where the polymer B) comprises, in [copolymerized] *polymerized* form, e) at least one α,β-ethylenically unsaturated monomer which additionally contains at least one group which is reactive toward isocyanate groups per molecule, *said at least one monomer being selected from the group consisting of:*

*esters of α,β-ethylenically unsaturated mono- and dicarboxylic acids with $C_1$–$C_{20}$-alkanediols, triols and polyols,*

*esters and amides of α,β-ethylenically unsaturated mono- and dicarboxylic acids with $C_2$–$C_{12}$-aminoalcohols which have a primary or secondary amino group, and*

*amides of α,β-ethylenically unsaturated mono- and dicarboxylic acids with di- and polyamines which have at least two primary or two secondary or one primary and one secondary amino group;* f) optionally at least one α,β-ethylenically unsaturated monomer which is chosen from esters of α,β-ethylenically unsaturated mono- and/or dicarboxylic acids with $C_1$- to $C_{22}$-alkanols, amides of α,β-ethylenically unsaturated mono- and/or dicarboxylic acids with mono- and di-$C_1$- to $C_{22}$-alkylamines, esters of vinyl alcohol and allyl alcohol with $C_1$- to $C_{40}$-monocarboxylic acids, vinyl ethers, aromatic vinyl compounds, vinyl halides, vinylidene halides, $C_2$- to $C_8$-monoolefins, nonaromatic hydrocarbons having at least 2 conjugated double bonds and mixtures thereof, g) optionally at least one α,β-ethylenically unsaturated monomer which is chosen [form] *from* N-vinylamides, N-vinyllactams, primary amides of α,β-ethylenically unsaturated monocarboxylic acids, vinyl- and allyl-substituted heteroaromatic compounds and mixtures thereof, h) optionally at least one further monomer containing a free-radically polymerizable, α,β-ethylenically unsaturated double bond and at least one ionogenic or ionic group per molecule,

[or a salt thereof] *or a salt thereof.*

2. A composition of claim 1 which is a coating composition for hair, skin and nails.

3. The composition of claim 1 comprising a) from 0.5 to 20% by weight of at least one water-soluble or -dispersible polyurethane as defined in claim 1 b) from 40 to 99% by weight of a solvent chosen from water and water-miscible solvents and mixtures thereof, c) from 0 to 50% by weight of a propellant, d) from 0 to 15% by weight of at least one water-soluble or -dispersible hair polymer which is different from a), e) from 0 to 0.2% by weight of at least one water-insoluble silicone, and f) from 0 to 2% by weight of at least one nonionic, siloxane-containing, water-soluble or -dispersible polymer.

4. A coating composition or binder for solid drug forms, which comprises at least one polyurethane of claim 1.

5. The composition of claim 1 where the polymer B) comprises, in copolymerized form, from 0.05 to 15% by weight of at least one component e), from 0 to 99.9% by weight of at least one component f), from 0 to 99.9% by weight of at least one component g), and from 0 to 50% by weight of at least one component h)

the total amount of components f) and g) being in a range from 30 to 99.9% by weight.

6. The composition of claim 1 where the component e) is an ester of acrylic acid or methacrylic acid with $C_2$- to $C_{12}$-aminoalcohol, where the amine nitrogen may additionally carry a $C_1$- to $C_8$-alkyl radical.

7. The composition of claim 1 where the ratio of NCO equivalent of the component A) to equivalent of active hydrogen atom of component B) is in a range from 20:1 to 1:1.

* * * * *